(12) United States Patent
Ruggeri et al.

(10) Patent No.: US 7,199,122 B2
(45) Date of Patent: Apr. 3, 2007

(54) METHODS FOR INHIBITING ANGIOGENESIS

(75) Inventors: Bruce A. Ruggeri, West Chester, PA (US); Margie L. Clapper, Harleysville, PA (US)

(73) Assignee: Fox Chase Cancer Center, Philadelphia, PA (US)

( * ) Notice: Subject to any disclaimer, the term of this patent is extended or adjusted under 35 U.S.C. 154(b) by 257 days.

(21) Appl. No.: 10/262,237

(22) Filed: Oct. 1, 2002

(65) Prior Publication Data

US 2003/0100564 A1 May 29, 2003

Related U.S. Application Data

(60) Provisional application No. 60/326,577, filed on Oct. 2, 2001.

(51) Int. Cl.
*A61K 31/495* (2006.01)
*A61K 31/4965* (2006.01)
*A61K 31/385* (2006.01)

(52) U.S. Cl. .................. 514/249; 514/255.05; 514/441
(58) Field of Classification Search ................ 514/249, 514/255.05
See application file for complete search history.

(56) References Cited

U.S. PATENT DOCUMENTS

| | | | | |
|---|---|---|---|---|
| 4,138,487 | A | 2/1979 | Barreau et al. | 424/250 |
| 5,571,523 | A | 11/1996 | Lee et al. | 424/423 |
| 5,668,117 | A | 9/1997 | Shapiro | 514/55 |
| 5,686,436 | A | 11/1997 | Van Dyke | 514/171 |
| 5,691,338 | A | 11/1997 | Prochaska et al. | 514/252 |
| 5,786,344 | A | 7/1998 | Ratain et al. | 514/100 |
| 6,812,248 | B2 * | 11/2004 | Zhang et al. | 514/514 |

FOREIGN PATENT DOCUMENTS

| | | |
|---|---|---|
| WO | WO 96/24694 | 8/1996 |
| WO | WO 96/28114 | 9/1996 |
| WO | WO 97/03055 | 1/1997 |
| WO | WO 98/27970 | 7/1998 |
| WO | WO 92/14456 | 9/2002 |

OTHER PUBLICATIONS

Cecil, Textbook of Medicine, 21st Edition, vol. 1, published 2000 by W.B. Saunders Company (PA), pp. 1061-1074.*
Ansher, S.S. et al., "Biochemical Effects of Dithiolthiones", *Fd Chem Toxic*, 1986, 24(5), 405-415.
Arbiser, J.L. et al., "The antiangiogenic agents TNP-470 and 2-methoxyestradiol inhibit the growth of angiosarcoma in mice", *Journal of the American Academy of Dermatology*, 1999, 40(6), Part 1, 925-929.
Arbiser, J.L. et al. "Oncogenic H-ras stimulates tumor angiogenesis by teo distinct pathways", *Proc. Natl. Acad. Sci. USA*, 1997, 94, 861-866.

Bernatchez, P.N. et al., "Vascular Endothelial Growth Factor Effect on Endothelial Cell Proliferation, Migration, and Platelet-activating Factor Synthesis is Flk-1-dependent", *The Journal of Biological Chemistry*, 1999, 274(43)31047-21054.
Bieder, A.et al., "Comparasion of the Metabolism of Oltipraz in the Mouse, Rat and Monkey and in Man", *Drug. Res.*, 1983, 33(11) No. 9, 1289-1297.
Bueding, E. et al., "The Antischistosomal Activity of Oltipraz", *Res. Comm. Chem. Path. Pharm.* 1982, 37(2), 293-303.
Brown, K.J. et al., "A Novel In Vitro Assay for Human Angiogenesis", *Laboratory Investigation*, 1996, 75(4), 539-555.
Clapper, M.L. et al., "Coordinate Induction of Glutathione S-Transferase β, μand π Expression in Murine Liver after a Single Administration of Olitipraz", *The American Society for Pharmacology and Experimental Therapeutics*, 1994, 45, 469-474.
Clapper, M.L. "Comprehensive Activity of Oltipraz", *Pharmacol. Ther.*, 1998, 78(1), 17-27.
Deplanque, G. et al., "Anti-angiogenic agents: clinical trial design and therapies in development", *European Journal of Cancer*, 2000, 36, 1713-1724.
Elmore, E. et al., "Correlation of Chemopreventive Efficacy Data from the Human Epidermal Cell Assay with *in vivo* Data", *Anticancer Research*, 2000, 20, 27-32.
Folkman, J. MD., "Tumor Angiogenesis", *Cancer Medicine*, 2000, 5th Edition, 132-152.
Fong, T.A.T. et al., "SU5416 Is a Potent and Selective Inhibitor of the Vascular Endothelial Growth Factor Receptor (Flk-1KDR) That Inhibits Tyrosine Kinase Catalysis, Tumor Vascularization, and Growth of Multiple Tumor Types", *Cancer Research*, 1999, 59, 99-106.
Gasparini, G. "The Rationale and Future Potential of Angiogenesis Inhibitors in Neoplasia", *Drugs*, 1999, 58(1), 17-38.
Greene, T.W. et al., *Protective Groups in Organic Synthesis*, 1991, 2nd Edition. Wiley & Sons.
Griffioen, A.W. et al., "Angiogenesis; Potentials for Pharmacologic Intervention in the Treatment of Cancer, Cardiovascular Diseases, and Chronic Inflammation", *Pharmacol. Rev.*, 2000, 52(2), 237-268.
Hanahan, D. "Signaling Vascular Morphogenisis and Maintenance", *Science*, 1997, 277, 48-50.
Heusse, D. et al., "Disposition of 14 C-Oltipraz in Animals", *Drug Res*, 1985, 35(II), 9, 1431-1436.
Ilan, N. et al., "Distinct signal transduction pathways are utilized during the tube formation and survival phases of in vitro angiogenesis", *Journal of Cell Science*, 1998, 111, 3621-3631.
Ingeber, D. et al., "Synthetic analogues of fumagillin that inhibit angiogenesis and suppress tumour growth", *Nature*, 1990, 348, 555-557.
Jain, R.K. et al., "Quantitative angiogenesis assays: Progress and problems", *Nature Medicine*, 1997, 3(11), 1203-1208.

(Continued)

*Primary Examiner*—Raymond J. Henley, III
(74) *Attorney, Agent, or Firm*—Dann, Dorfman, Herrell and Skillman, P.C.; Patrick J. Hagan, Esq.

(57) ABSTRACT

Novel methods for inhibiting angiogenesis and treating diseases associated with angiogenesis are described. The methods may comprise administering to a patient an effective amount of a 1,2-dithiol-3-thione derivative or metabolite thereof. Preferred compounds for use in the methods include 5-(2-pyrazinyl)-4methyl-1,2-dithiol-3-thione (Oltipraz) and its metabolites.

32 Claims, 4 Drawing Sheets

OTHER PUBLICATIONS

Jones, M.K. et al., "Inhibition of angiogenesis by nonsteroidal anti-inflammatory drugs: Insight into mechanisms and implications for cancer growth and ulcer healing", *Nature Medicine*, 1999, 5(12), 1418-1423.

Kensler, T.W. et al., "Olitpraz: Clinical Opportunities for Cancer Chemoprevention", *Journal of Cellular Biochemistry*, 1995, 22, 101-107.

Kensler, T.W. et al., "Mechanism of Protection against Aflatoxin Tumorigenicity in Rats Fed 5-(2-Pyrazinyl)-4-methyl-1,2-dithiol-3-thione(Oltipraz) and Related 1,2-Dithiol-3-thiones and 1,2-Dithiol-3-ones", *Cancer Research*, 1987, 47, 4271-4277.

Laird, A.D. et al., "SU6668 is a Potent Antiangiogenic and Antitumor Agent That Induces Regression of Established Tumors", *Cancer Research*, 2000, 60, 4152-4160.

Liekens, S. et al., "A Novel Animal Model for Hemangiomas: Inhibition of Hemangioma Development by the Angiogenesis Inhibitor TNP-470", *Cancer Research*, 1999, 59, 2376-2383.

Liu, Y.I. et al., "Protection by 5-(2-Pyrazinyl)-4-methyl-1, 2-dithiol-3-thione(Oltipraz) against the Hepatotoxicity of Alflatoxin B1 in the Rat", *Toxicology and Applied Pharmacology*, 1988, 93, 442-451.

Malinda, K.M. et al., "Identification of laminin α1 and β1 chain peptides active for endothelial cell adhesion, tube formation, and aortic sprouting", *The FASAB Journal*, 1999, 13, 53-62.

Masferrer, J.L. et al., "Antiangiogenic and ANtitumor Activities of Cyclooxygenase-2 Inhibitors", *Cancer Research*, 2000, 60, 1306-1311.

Montesano, R. et al., "In vitro Rapid Organization of Endothelial Cells into Capillary-like Networks is Promoted by Collagen Matrices", *The Journal of Cell Biology*, 1983, 97, 1648-1652.

Nicosia, R.F. et al., "Endogenous Regulation of Angiogenesis in the Rat Aorta Model", *American Journal of Pathology*, 1997, 151(5), 1379-1386.

Nicosia, R.F. et al., "Autoregulation of Angiogenesis by Cells of the Vessel Wall", *International Review of Cytology*, 1999, 185, 1-43.

O'Dwyer, P.J. et al., "The Chemopreventive Agent Oltipraz Stimulates Repair of Damaged DNA", *Cancer Research*, 1997, 57, 1050-1053.

O'Dwyer, P.J. et al., "Cellular Kinetics of Induction by Oltipraz and Its Keto Derivative of Detoxication Enzymes in Human Colon Adenocarcinoma Cells", *Clin. Cancer Research*, 1997, 3, 783-791.

Passaniti, A. et al., "Methods in Laboratory Investigation," A Simple, Quantitative Method for Assessing Angiogenesis and Antiangiogenice Agents Using Reconstituted Basement Membrane, Heparin, and fibroblast Growth Factor, *Laboratory Investigation*, 1992, 67(4), 519-528.

Plunkett, M.L. et al., "Methods in Laboratory Investigation, A In vivo Quantitative Angiogenesis Model Using Tumor Cells Entrapped in Alginate", *Laboratory Investigation*, 1990, 62(4), 510-517.

*Remington's Pharmaceutical Sciences* (Mack Pub. Co., Easton Pa.), 1980.

Smith, W.A. et al., "Modulation of dibenzol[a}pyrene-DNA-adduction by chemopreventive agents in the human breast epithelial cell line MCF-7", *Proc. Am. Assoc. Cancer. Res.*, 1997, 38, 362.

Sun, L. et al.,"Synthesis and Biological Evaluations of 3-Substituted Indolin-2-ones: A Novel Class of Tyrosine Kinase Inhibitors That Exhibit Selectivity toward Particular Receptor Tyrosine Kinases", *J. Med. Chem.*, 1998, 2588-2603.

Wedge, S.R. et al.,"D4190: Am Orally Active Inhibitor of Vascular Endothelial Growth Factor Signaling with Broad-Spectrum Antitumor Efficacy", *Cancer Research*, 2000, 60, 970-975.

Wood, J.M. et al., "PTK787/ZK 222584, a Novel and Potent Inhibitor of Vascular Endothelial Growth Fcotr Receptor Tyrosine Kinases, Impairs Vascular Endothelial Growth Factor-induced Responses and Tumor Growth after Oral Administration", *Cancer Research*, 2000, 60, 2178-2189.

Zhu, W-H. et al., "Regulation of Vascular Growth and Regression by Matrix Metalloproteinases in the Rat Aorta Model of Angiogenesis" *Laboratory Investigation*, 2000, 80(4), 545-555.

Invitation to Pay Additional Fees dated Jun. 23, 2003 (PCT/US-02/31353).

Database WPI, *Derwent Publications Ltd.*, London, GB, JP 07 112978 A (Mitsui Toatsu Chem. Inc.), May 2, 1995, XP 002241164 (abstract).

Ruggeri, B.A., et al., "The chemopreventive agent oltipraz possesses potent antiangiogenic activity in vitro, ex vivo, and in vivo and inhibits tumor xenograft growth," *Clinical Cancer Res.*, Jan. 2002, 8, 267-274.

Wilkinson, J., et al., "Effect of oltipraz on the expression multiple genes (n=588) in ICR/HA mice," *Fox Chase Cancer Center*, Philadelphia, Mar. 1999, 40, XP-001147462, (abstract), 1 page.

* cited by examiner

METHODS FOR INHIBITING ANGIOGENESIS

CROSS REFERENCE TO RELATED APPLICATIONS

This application claims priority of U.S. provisional application Ser. No. 60/326,577, filed Oct. 2, 2001, the disclosure of which is incorporated herein by reference in its entirety.

GOVERNMENT INTERESTS

This invention was funded in part by the National Institutes of Health. The United States government may have certain rights in this invention.

FIELD OF THE INVENTION

The present invention relates to novel chemotherapeutic methods. More particularly, the present invention relates to novel methods for inhibiting angiogenesis by using derivatives or metabolites of 1,2-dithiol-3-thiones.

BACKGROUND OF THE INVENTION

Throughout this application, various publications are referenced by arabic numerals within parentheses. Full citations for these publications may be found at the end of the specification immediately preceding the claims. The disclosure of these publications in their entireties are hereby incorporated by reference herein to more fully describe the state of the art as known to those skilled therein as of the date of the invention described and claimed herein.

Epidemiological and experimental evidence has shown that consumption of diets high in certain vegetables, such as cabbage and other members of the family Cruciferae, may reduce the incidence of certain cancers. These vegetables typically contain dithiolthiones, which are sulfur-containing compounds that have been associated with a number of biochemical changes. The most notable of these changes include increases in the activities of enzymes catalyzing the inactivation of toxic compounds, including carcinogens, and increases in tissue reduced glutathione (GSH) levels (10). Certain synthetic dithiolthiones, for example substituted 1,2-dithiol-3-thiones, are also known to be useful medicinally as antischistosomal agents, choleretics, and to stimulate salivary secretion (6, 8, 10). The preparation and use of such compounds as pharmaceutical compositions is described, for example, in U.S. Pat. No. 4,138,487, the disclosure of which is incorporated herein by reference in its entirety.

Oltipraz (5-(2-pyrazinyl)-4-methyl-1,2-dithiol-3-thione) is a synthetic dithiolthione with physiochemical properties similar to those of dithiolthione antioxidants typically found in cruciferous vegetables (6). Based upon these properties, Oltipraz, and other 1,2-dithiol-3-thione derivatives have been studied for use as potential chemopreventive agents (10–15). Chemoprevention refers to the use of natural or synthetic agents to inhibit carcinogenesis. The development of chemopreventive agents is focused on identifying agents that prevent or inhibit the intracellular changes that may induce tumor formation or lead to the formation of pre-neoplastic lesions. This may be contrasted with the development of chemotherapeutic agents, which is focused upon identifying agents that may lead to the regression of existent neoplasms, and/or prevent the further growth or metastasis of tumors. Chemopreventive agents may work, for example, to detoxify carcinogenic compounds, or to protect genetic material from changes that may be associated with the initiation of cancer. Preclinical evaluation of Oltipraz has demonstrated its broad efficacy in preventing carcinogen-induced rodent tumors in multiple organ sites, including the breast, bladder, colon, stomach, liver, lymph nodes, lung, pancreas, and skin (6, 7). Clinical studies on the initial use of Oltipraz as an anti-schistosomal agent (8), and in more recent phase I and II trials in patient populations susceptible for cancer of the colon, breast, liver, and lung (reviewed in Ref. 7), have also revealed its minimal toxicity in man.

The significant chemopreventive activity of Oltipraz in vivo (7) and in vitro (9) has been attributed primarily to its pronounced induction of a battery of phase II detoxification enzymes (10–13) and its activity in decreasing the formation of DNA-carcinogen adducts in vitro and in vivo (11, 14–16). Most of the chemoprevention protocols tested to date have involved concomitant exposure of the test subject to both carcinogen and Oltipraz (6). Complete protection against aflatoxin $B_1$ has been achieved when Oltipraz is fed both before and during carcinogen administration. However, administration of the drug after exposure to aflatoxin $B_1$ was observed to have no chemopreventive effect (6). The prevention of initiation of azoxymethane-induced colon carcinogenesis by Oltipraz has been shown to be nearly equi-effective, regardless of whether the drug was administered during or after carcinogen administration, further suggesting that Oltipraz may inhibit the induction of cancer by more than one mechanism.

To date, little if any evidence exists to suggest that substituted 1,2-dithiol-3-thiones such as Oltipraz may be useful as chemotherapeutic agents for treating neoplastic conditions, however. Although it has been shown in the Syrian hamster model of N-nitrosobis(2-oxopropyl)-amine (BOP)-induced ductal pancreatic carcinoma that concurrent administration of BOP and Oltipraz may lead to a prolonged survival rate in animals that develop BOP-induced metastatic disease (7), there has previously been no evidence to suggest that compounds such as Oltipraz may be used therapeutically to inhibit tumor growth or metastasis, or to induce regression of established tumors.

Angiogenesis, the formation of new blood vessels out of pre-existing capillaries, is a sequence of events that is of key importance in a broad array of physiologic and pathologic processes. Normal tissue growth, such as in embryonic development, wound healing, and the menstrual cycle, is characterized by dependence on new vessel formation for the supply of oxygen and nutrients as well as removal of waste products. A large number of different and unrelated diseases are also associated with formation of new vasculature. Among certain pathologies are conditions in which angiogenesis is low, and should be enhanced to improve disease conditions. More frequently, however, excessive angiogenesis is an important characteristic of various pathologies, including pathologies characterized or associated with an abnormal or uncontrolled proliferation of cells. Pathologies which involve excessive angiogenesis include, for example, cancer (both solid and hematologic tumors), cardiovascular diseases (such as atherosclerosis and restenosis), chronic inflammation (rheumatoid arthritis, Crohn's disease), diabetes (diabetic retinopathy), psoriasis, endometriosis, neovascular glaucoma and adiposity (3). These conditions may benefit from chemotherapeutic inhibition of angiogenesis.

Generally speaking, the angiogenic process entails the proliferation and migration of a normally quiescent endothelium, the controlled proteolysis of the pericellular matrix, and the synthesis of new extracellular matrix components by developing capillaries. The establishment of new intra- and intercellular contacts and the morphological differentiation of endothelial cells to capillary-like tubular networks provide support for their subsequent maturation, branching, remodeling and selective regression to form a highly organized, functional microvascular network. The autocrine, paracrine and amphicrine interactions of the vascular endothelium with its surrounding stromal components, as well as with the pro-angiogenic and angiostatic cytokines and growth factors orchestrating physiologic angiogenesis, are normally tightly regulated both spatially and temporally (1–4).

Angiogenesis is crucial to the growth of neoplastic tissues (4). For more than 100 years, tumors have been observed to be more vascular than normal tissues. Several experimental studies have suggested that both primary tumor growth and metastasis require neovascularization (1). In contrast to the well orchestrated process described above for normal tissue growth, the pathologic angiogenesis necessary for active tumor growth is generally sustained and persistent, with the initial acquisition of the angiogenic phenotype being a common mechanism for the development of a variety of solid and hematopoietic tumor types (1–4). Tumors that are unable to recruit and sustain a vascular network typically remain dormant as asymptomatic lesions in situ (4). Metastasis is also angiogenesis-dependent: for a tumor cell to metastasize successfully, it generally must gain access to the vasculature in the primary tumor, survive the circulation, arrest in the microvasculature of the target organ, exit from this vasculature, grow in the target organ, and induce angiogenesis at the target site. Thus, angiogenesis appears to be necessary at the beginning as well as the completion of the metastatic cascade (4).

The criticality of angiogenesis to the growth and metastasis of neoplasms thus provides an optimal potential target for chemotherapeutic efforts. Appropriate anti-angiogenic agents may act directly or indirectly to influence tumor-associated angiogenesis either by delaying its onset (i.e., blocking an "angiogenic switch") or by blocking the sustained and focal neovascularization that is characteristic of many tumor types. Anti-angiogenesis therapies directed against the tumor-associated endothelium and the multiple molecular and cellular processes and targets implicated in sustained pathologic angiogenesis are being actively evaluated for their safety and efficacy in multiple clinical trials (reviewed in Ref. 1, 4 and 5). However, there has been limited success to date with the discovery and/or identification of safe and/or effective anti-angiogenic agents.

Accordingly, new and/or better anti-angiogenic agents and/or methods for inhibiting angiogenesis are needed. The present invention is directed to these, as well as other, important ends.

SUMMARY OF THE INVENTION

The present invention is directed, in part, to novel methods for inhibiting angiogenesis. Specifically, in one embodiment, there are provided novel methods for inhibiting angiogenesis comprising administering to a patient an effective amount of a compound of the following formula (I):

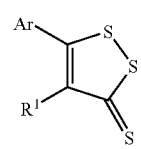

(I)

wherein:
Ar is a monocyclic or bicyclic aryl group or a monocyclic or bicyclic heteroaryl group containing 1 to 3 —O—, —S— or —N($R^2$) heteroatoms; and
$R^1$ and $R^2$ are independently hydrogen or an alkyl group; or a stereoisomer, prodrug, metabolite, or pharmaceutically acceptable salt, hydrate or N-oxide thereof.

Another embodiment of the invention relates to methods of inhibiting angiogenesis comprising administering to the patient an effective amount of a 1,2-dithiol-3-thione derivative or a metabolite thereof.

Yet another embodiment of the invention relates to methods for inhibiting the growth or metastasis of a tumor comprising administering to a patient an effective amount of an anti-angiogenic agent, wherein the anti-angiogenic agent comprises a compound of the following formula (I):

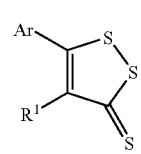

(I)

wherein:
Ar is a monocyclic or bicyclic aryl group or a monocyclic or bicyclic heteroaryl group containing 1 to 3 —O—, —S— or —N($R^2$) heteroatoms; and
$R^1$ and $R^2$ are independently hydrogen or an alkyl group; or a stereoisomer, prodrug, metabolite, or pharmaceutically acceptable salt, hydrate or N-oxide thereof.

Still another embodiment of the invention relates to methods for inhibiting the growth or metastasis of a tumor, comprising administering to a patient an effective amount of an anti-angiogenic agent, wherein the anti-angiogenic agent comprises a 1,2-dithiol-3-thione derivative or a metabolite thereof.

Yet another embodiment of the invention relates to methods for treating a disease associated with angiogenesis comprising administering to the patient an effective amount of an anti-angiogenic agent, wherein said anti-angiogenic agent comprises a compound of the following formula (I):

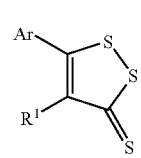

(I)

wherein:
Ar is a monocyclic or bicyclic aryl group or a monocyclic or bicyclic heteroaryl group containing 1 to 3 —O—, —S— or —N($R^2$) heteroatoms; and $R^1$ and $R^2$ are independently hydrogen or an alkyl group; or a stereoisomer, prodrug, metabolite, or pharmaceutically acceptable salt, hydrate or N-oxide thereof.

A further embodiment of the invention relates to methods for treating a disease or disorder associated with angiogenesis comprising administering to the patient an effective amount of an anti-angiogenic agent, wherein said anti-angiogenic agent comprises a 1,2-dithiol-3-thione derivative or a metabolite thereof.

These and other aspects of the invention will become more apparent from the following detailed description.

DETAILED DESCRIPTION OF THE INVENTION

Figure 1A:
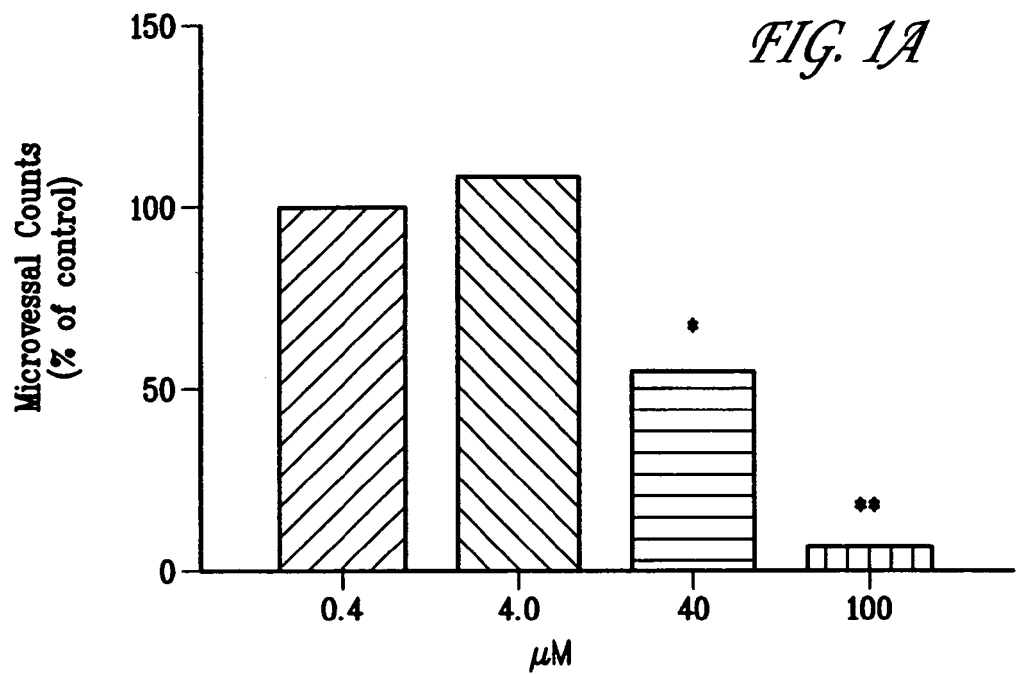
FIG. 1. Effect of Oltipraz on angiogenesis in collagen gel cultures of rat aortic ring explants at day 8, the peak of growth of microvessels. A. Oltipraz was added to rings in serum-free media at four concentrations. Values are the means of 4 replicates from two independent assays. Variation in microvessel number was ±5–7% across replicates. *=$p<0.05$, **=$p<0.01$ by Dunnet's Multiple Comparison test. B. Light microscopy photographs of rat aortic ring explant cultures during the peak phase of microvessel growth. Shown are vehicle-treated control cultures (left panel) and cultures treated with 40 µM Oltipraz (right panel). Magnification×100.

As employed above and throughout the disclosure, the following terms, unless otherwise indicated, shall be understood to have the following meanings.

"Alkyl" refers to an aliphatic hydrocarbon group which may be straight, branched or cyclic having from 1 to about 10 carbon atoms in the chain, and all combinations and subcombinations of ranges therein. "Branched" refers to an alkyl group in which a lower alkyl group, such as methyl, ethyl or propyl, is attached to a linear alkyl chain. In certain preferred embodiments, the alkyl group is a $C_1$–$C_4$ alkyl group, i.e., a branched or linear alkyl group having from 1 to about 4 carbons. In other preferred embodiments, the alkyl group is a $C_1$–$C_3$ alkyl group, i.e., a branched or linear alkyl group having from 1 to about 3 carbons. Exemplary alkyl groups include methyl, ethyl, n-propyl, isopropyl, butyl, isobutyl, sec-butyl, tert-butyl, pentyl, hexyl, heptyl, octyl, nonyl and decyl.

"Aryl" refers to an aromatic carbocyclic radical containing from about 6 to about 10 carbons, and all combinations and subcombinations of ranges therein. The aryl group may be optionally substituted with one or two or more aryl group substituents. Preferred aryl group substituents include halo, alkyl, alkoxy, mercapto, amino, monoalkylamino, alkylthio, dialkylamino, pyrrolidinyl, piperidinyl, morpholinyl or 4-alkylpiperazinyl groups. Exemplary aryl groups include monocyclic groups, such as phenyl, and bicyclic groups, such as naphthyl.

"Heteroaryl" refers to an aromatic carbocyclic radical containing from about 4 to about 10 members, and all combinations and subcombinations of ranges therein, wherein one or more of the members is an element other than carbon, for example, nitrogen, oxygen or sulfur. The heteroaryl group may be optionally substituted with one or two or more heteroaryl group substituents, including the aryl group substituents described above. Exemplary heteroaryl groups include monocylic groups, such as pyridyl, and bicyclic groups, such as indolyl.

"Halo" refers to fluoro, chloro or bromo.

"Alkoxy" refers to an alkyl-O— group where alkyl is as previously described. Exemplary alkoxy groups include, for example, methoxy, ethoxy, propoxy, butoxy and heptoxy.

"Alkylthio" refers to an alkyl-S— group wherein alkyl is as previously described. Exemplary alkylthio groups include methylthio, ethylthio, i-propylthio and heptylthio.

"Monoalkylamino" refers to an -NHR group wherein R is an alkyl group as previously described. Exemplary monoalkylamino groups include methylamino and ethylamino.

"Dialkylamino" refers to an -NRR' group wherein each of R and R' is independently an alkyl group as previously described. Exemplary dialkylamino groups include ethylmethylamino, dimethylamino and diethylamino.

"Effective amount" refers to an amount of a compound as described herein that may be therapeutically effective to inhibit growth or metastasis of an existing tumor. Such therapeutically effective activity may be achieved, for example, by contacting cells, tissues and/or receptors with compounds of the present invention.

"Pharmaceutically acceptable" refers to those compounds, materials, compositions, and/or dosage forms which are, within the scope of sound medical judgment, suitable for contact with the tissues of human beings and animals without excessive toxicity, irritation, allergic response, or other problem complications commensurate with a reasonable benefit/risk ratio.

"Pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

Certain acidic or basic compounds of the present invention may exist as zwitterions. All forms of the compounds, including free acid, free base and zwitterions, are contemplated to be within the scope of the present invention.

In the formulas described and claimed herein, it is intended that when any symbol appears more than once in a particular formula or substituent, its meaning in each instance is independent of the other.

"Patient" refers to animals, including mammals, preferably humans.

"Metabolite" refers to any substance resulting from chemical changes involved in the processes of growth and repair in a living organism, including the anabolic and catabolic processes.

In certain embodiments, the present invention is directed to methods for inhibiting angiogenesis and/or inhibiting the growth or metastasis of a tumor. As used herein, the term "inhibit" means that the amount of tumor growth or metastasis and/or the occurrence of angiogenesis in patients that have received a compound, as described herein, may be desirably reduced as compared to patients that have not received that compound. Thus, in preferred form, the inhibitory methods of the present invention comprise administering to a patient an effective amount of an anti-angiogenic agent. The term "anti-angiogenic agent", as used herein, refers to compounds which may inhibit angiogenesis.

In other embodiments, the invention is directed to methods for treating a disease or disorder associated with angiogenesis. These methods may preferably include the step of identifying a patient having such a disease, including patients who would benefit from the treatment methods described herein. Diseases or disorders associated with angiogenesis include, for example, conditions in which angiogenesis plays a role in the pathology or progression of the condition, such that inhibition of angiogenesis in a patient having such a condition may delay or prevent the further progression of the condition, or lead to remission or regression of the disease state. Such conditions are frequently characterized by or associated with abnormal cellular proliferation and include, for example, neoplastic diseases. As used herein, the term "treating a disease or disorder" refers to the administration of agents intended to limit the extent, progression and/or severity of a condition in a patient, as compared to patients that have not been so treated. As used herein, the term "neoplastic disease" refers to any condition characterized by the presence of an aberrant growth of abnormal cells or tissue, including, but not limited to all cancers and tumors, whether benign or malignant. "Treating neoplastic disease" refers to the administration of a chemotherapeutic agent that will inhibit the further growth or metastasis of any neoplastic tissue that may exist in a patient and/or stimulate regression of such neoplasms, including reducing the size and/or number of such neoplasms and/or inducing the death of neoplastic cells.

In preferred embodiments, the present methods involve administering to a patient a 1,2-dithiol-3-thione derivative or a metabolite thereof. The term "1,2-dithiol-3-thione derivative", as used herein, refers to a compound which includes a 1,2-dithiol-3-thione moiety, namely:

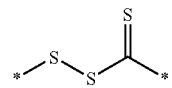

where "*" refers to the point of attachment of the 1,2-dithiol-3-thione moiety to the remainder of the compound. Exemplary 1,2-dithiol-3-thione derivatives include, inter alia, 4-phenyl-1,2,dithiol-3-thione, 5-phenyl-1,2,dithiol-3-thione, 5-(p-methoxyphenyl)-1,2-dithiol-3-thione (Anethole Dithiolthione), 5-(m-methoxyphenyl)-1,2-dithiol-3-thione 5-(2-pyrazinyl)-1,2-dithiol-3-thione (ADT), and 5-(2-pyrazinyl)-4-methyl-1,2-dithiol-3-thione (Oltipraz).

In preferred form, the 1,2-dithiol-3-thione derivative is a compound of the following formula (I):

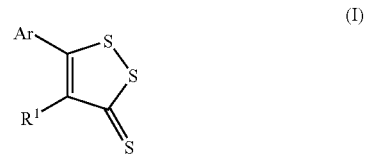

(I)

wherein:

Ar is a monocyclic or bicyclic aryl group or a monocyclic or bicyclic heteroaryl group containing 1 to 3 —O—, —S— or —N($R^2$) heteroatoms; and $R^1$ and $R^2$ are independently hydrogen or an alkyl group; or a stereoisomer, prodrug, metabolite, or pharmaceutically acceptable salt, hydrate or N-oxide thereof.

In the above compound of formula (I), $R^1$ is hydrogen or alkyl. Preferably, $R^1$ is hydrogen.

In the above compound of formula (I), Ar is a monocyclic or bicyclic aryl group or a monocyclic or bicyclic heteroaryl group. Preferred aryl groups include phenyl and naphthyl, with phenyl being more preferred. Preferred heteroaryl groups contain 1 to 3 —O—, —S— or —N($R^2$) heteroatoms. Even more preferred heteroaryl groups contain 1 to 2 —N($R^2$) heteroatoms. In particularly preferred embodiments, Ar is a monocyclic heteroaryl group selected from the group consisting of pyridyl, pyridazinyl, pyrimidinyl and pyrazinyl, with pyrazinyl being especially preferred.

The group $R^2$ in the definition of Ar is hydrogen or alkyl. More preferably, $R^2$ is hydrogen.

In a particularly preferred embodiment, the compound of formula (I) is 5-(2-pyrazinyl)-4-methyl-1,2-dithiol-3-thione (Oltipraz).

The 1,2-dithiol-3-thione derivatives useful in the methods of the present invention are preferably anti-schistosomal agents. The term "anti-schistosomal agent", as used herein, refers to compounds which may inhibit schistosomiasis.

In an alternate embodiment, the methods of the present invention may involve administering to a patient a metabolite of a 1,2-dithiol-3-thione derivative. Oltipraz is extensively metabolized in vivo (26). As many as thirteen metabolites of Oltipraz have been identified, and several have been found to be just as active as the parent compound (7, 33).

In preferred form, the metabolites have the following formula (II):

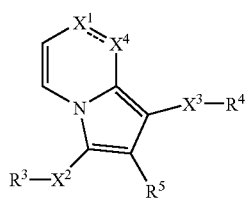
(II)

wherein:

$X^1$ is $C(R^6)_y$ or $N(R^7)_n$ in which y is an integer 1 or 2, and n is an integer 0 or 1;

$X^2$ and $X^3$ are each independently —O—, —S(O)$_x$— where x is an integer 0, 1 or 2, or —N(R$^8$);

$X^4$ is $C(R^6)_y$ or C(=O), in which y is an integer 1 or 2;

$R^3$ is hydrogen, alkyl, the residue of glucuronic acid, or the radical

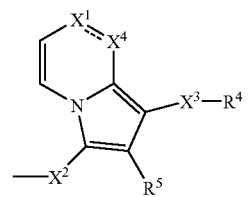

$R^4$, $R^5$ and $R^6$ are each independently hydrogen or alkyl;
$R^7$ is hydrogen or the residue of glucuronic acid; and
$R^8$ is hydrogen or alkyl.

In the above compound of formula (II), $X^1$ is $C(R^6)_y$ or $N(R^7)_n$ in which y is an integer 1 or 2, and n is an integer 0 or 1. Preferably, $X^1$ is N.

In the above compound of formula (II), $X^2$ and $X^3$ are each independently —O—, —S(O)$_x$— where x is an integer 0, 1 or 2, or —N(R$^8$) heteroatoms. Preferably, $X^2$ and $X^3$ are —S—.

In the above compound of formula (II), $X^4$ is $C(R^6)_y$ or C(=O), in which y is an integer 1 or 2. Preferably, $X^4$ is $C(R^6)$.

In the above compound of formula (H), the dashed line represents a single or double bond, depending on the particular definitions selected for $X^1$ and $X^4$.

In the above compound of formula (II), $R^3$ is hydrogen, alkyl, the residue of glucuronic acid (i.e., a chemical group or moiety which is derived from glucuronic acid), or the radical

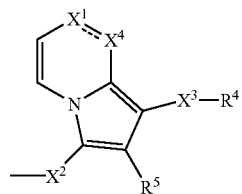

Preferably, $R^3$ is alkyl, with methyl being more preferred.

Also in the above compound of formula (II), $R^4$, $R^5$, $R^6$ and $R^8$ are each independently hydrogen or alkyl. Preferably, $R^4$, $R^5$ are alkyl, with methyl being particularly preferred. Preferably, $R^6$ and $R^8$ are hydrogen.

In the above compound of formula (II), $R^7$ is hydrogen or the residue of glucuronic acid.

In particularly preferred embodiments, the compound of formula (II) is selected from the following compounds:

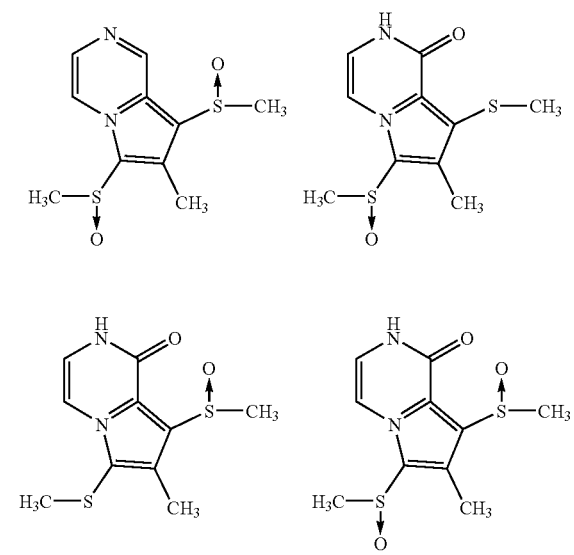

-continued

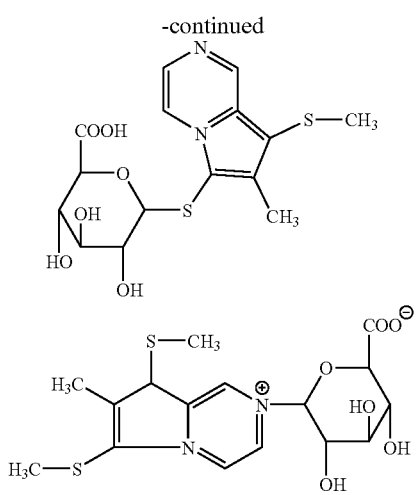

Preferred among these compounds is the compound of the formula

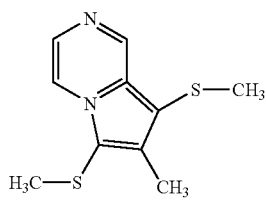

Further descriptions of these metabolites, and proposed mechanisms for the conversion of Oltipraz thereto, are set forth in WO 97/03055 and Bieder et al., Arzneim. Forsh. 33:1289–1297 (1983), the disclosures of which are hereby incorporated herein by reference, in their entireties.

As stated above, the present invention is based, inter alia, on the surprising and unexpected discovery that 1,2-dithiol-3-thione derivatives and/or metabolites thereof are potent and effective anti-angiogenic agents. Thus, the compounds described herein may be useful in the treatment and/or inhibition of diseases or disorders associated with angiogenesis. Disease conditions or disorders which may benefit from the inhibition of angiogenesis include: cancer; cardiovascular diseases (such as atherosclerosis and restenosis); chronic inflammation (rheumatoid arthritis, Crohn's disease); diabetes (diabetic retinopathy); psoriasis; endometriosis; ocular disorders (retinopathy, macular degeneration, neovascular glaucoma) and adiposity (3). Additionally, the methods for inhibiting angiogenesis, as described herein, are particularly useful for inhibiting the growth and/or metastasis of a tumor and for treating a patient having a neoplastic disease. Types of tumors which may benefit from treatment with anti-angiogenic agents include a variety of solid tumors, including gliomas, lipomas, hemangiomas, hemangioblastomas, papillomas, melanomas, carcinomas, lymphomas and sarcomas of multiple tissue and organ types, as well as a variety of hematological malignancies in which angiogenesis has been implicated, including acute myeloid leukemia (AML), acute lymphocytic leukemia (ALL), chronic lymphocytic leukemia (CLL), Chronic Myelogenous Leukemia (CML) and multiple myeloma.

The compounds employed in the methods of the present invention may exist in prodrug form. As used herein, the term "prodrug" is intended to include any covalently bonded carriers which release the active parent drug according to formulas (I) or (II) or other formulas or compounds employed in the methods of the present invention in vivo when such prodrug is administered to a mammalian subject. Since prodrugs are known to enhance numerous desirable qualities of pharmaceuticals (e.g., solubility, bioavailability, manufacturing, etc.), the compounds employed in the present methods may, if desired, be delivered in prodrug form. Thus, the present invention contemplates methods of delivering prodrugs. Prodrugs of the compounds employed in the present invention may be prepared by modifying functional groups present in the compound in such a way that the modifications are cleaved, either in routine manipulation or in vivo, to the parent compound.

Accordingly, prodrugs include, for example, compounds described herein in which a hydroxy, thiol, amino, or carboxy group is bonded to any group that, when the prodrug is administered to a mammalian subject, cleaves to form a free hydroxyl, thiol, free amino, or carboxylic acid, respectively. Examples include, but are not limited to, acetate, formate and benzoate derivatives of alcohol, thiol, and amine functional groups; and alkyl, carbocyclic, aryl, and alkylaryl esters such as methyl, ethyl, propyl, iso-propyl, butyl, isobutyl, sec-butyl, tert-butyl, cyclopropyl, phenyl, benzyl, and phenethyl esters, and the like.

The compounds employed in the methods of the present invention may be prepared in a number of ways well known to those skilled in the art. The compounds can be synthesized, for example, by the methods described below, or variations thereon as appreciated by the skilled artisan. All processes disclosed in association with the present invention are contemplated to be practiced on any scale, including milligram, gram, multigram, kilogram, multikilogram or commercial industrial scale.

As discussed in detail above, compounds employed in the present methods may contain one or more asymmetrically substituted carbon atoms, and may be isolated in optically active or racemic forms. Thus, all chiral, diastereomeric, racemic forms and all geometric isomeric forms of a structure are intended, unless the specific stereochemistry or isomeric form is specifically indicated. It is well known in the art how to prepare and isolate such optically active forms. For example, mixtures of stereoisomers may be separated by standard techniques including, but not limited to, resolution of racemic forms, normal, reverse-phase, and chiral chromatography, preferential salt formation, recrystallization, and the like, or by chiral synthesis either from chiral starting materials or by deliberate synthesis of target chiral centers.

As will be readily understood, functional groups present may contain protecting groups during the course of synthesis. Protecting groups are known per se as chemical functional groups that can be selectively appended to and removed from functionalities, such as hydroxyl groups and carboxyl groups. These groups are present in a chemical compound to render such functionality inert to chemical reaction conditions to which the compound is exposed. Any of a variety of protecting groups may be employed with the present invention. Preferred protecting groups include the benzyloxycarbonyl group and the tert-butyloxycarbonyl group. Other preferred protecting groups that may be employed in accordance with the present invention may be described in Greene, T. W. and Wuts, P. G. M., Protective Groups in Organic Synthesis 2d. Ed., Wiley & Sons, 1991.

1,2-Dithiol-3-thione derivative compounds according to the present invention may be synthesized employing methods taught, for example, in in U.S. Pat. No. 4,138,487, the disclosures of which are hereby incorporated herein by reference, in their entireties. Metabolites of 1,2-dithiol-3-thione derivative compounds useful in the methods according to the present invention may be synthesized employing methods taught, for example, in WO 97/03055, the disclosures of which are hereby incorporated herein by reference, in their entireties.

The compounds employed in the methods of the present invention may be administered by any means that results in the contact of the active agent with the agent's site of action in the body of a patient. The compounds may be administered by any conventional means available for use in conjunction with pharmaceuticals, either as individual therapeutic agents or in a combination of therapeutic agents. For example, they may be administered as the sole active agent in a pharmaceutical composition, or they can be used in combination with other therapeutically active ingredients. Other suitable therapeutically active ingredients include, for example, analgesics, anti-infectives, anti-allergics, hormones, genetic materials, peptides, beta-agonists, steroids, cholinergic agents, anti-cholinergic agents, 5-lipoxygenase inhibitors, leukotriene inhibitors, anti-neoplastic agents, antibiotics, anti-tumor drugs, radiation sensitizers, thrombolytic agents, anti-histamines, anti-coagulants, anti-inflammatories, hormones, growth factors and mitotic inhibitors.

The compounds are preferably combined with a pharmaceutical carrier selected on the basis of the chosen route of administration and standard pharmaceutical practice as described, for example, in *Remington's Pharmaceutical Sciences* (Mack Pub. Co., Easton, Pa., 1980), the disclosures of which are hereby incorporated herein by reference, in their entireties.

Compounds of the present invention can be administered to a mammalian host in a variety of forms adapted to the chosen route of administration, e.g., orally or parenterally. Parenteral administration in this respect includes administration by the following routes: intravenous, intramuscular, subcutaneous, rectal, intraocular, intrasynovial, transepithelial including transdermal, ophthalmic, sublingual and buccal; topically including ophthalmic, dermal, ocular, rectal, and nasal inhalation via insulation aerosol. The compounds may also be injected directly into a tumor mass.

The active compound may be orally administered, for example, with an inert diluent or with an assimilable edible carrier, or it may be enclosed in hard or soft shell gelatin capsules, or it may be compressed into tablets, or it may be incorporated directly with the food of the diet. For oral therapeutic administration, the active compound may be incorporated with excipient and used in the form of ingestible tablets, buccal tablets, troches, capsules, elixirs, suspensions, syrups, wafers, and the like. Such compositions and preparations should preferably contain at least about 0.1% of active compound. The percentage of the compositions and preparations may, of course, be varied and may conveniently be, for example, from about 2 to about 6% of the weight of the unit. The amount of active compound in such therapeutically useful compositions is preferably such that a suitable dosage will be obtained. Preferred compositions or preparations according to the present invention may be prepared so that an oral dosage unit form contains from about 0.1 to about 1000 mg of active compound, and all combinations and subcombinations of ranges and specific amounts therein.

The tablets, troches, pills, capsules and the like may also contain one or more of the following: a binder, such as gum tragacanth, acacia, corn starch or gelatin; an excipient, such as dicalcium phosphate; a disintegrating agent, such as corn starch, potato starch, alginic acid and the like; a lubricant, such as magnesium stearate; a sweetening agent such as sucrose, lactose or saccharin; or a flavoring agent, such as peppermint, oil of wintergreen or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavoring, such as cherry or orange flavor. Of course, any material used in preparing any dosage unit form is preferably pharmaceutically pure and substantially non-toxic in the amounts employed. In addition, the active compound may be incorporated into sustained-release preparations and formulations.

The active compound may also be administered parenterally or intraperitoneally. Solutions of the active compound as a free base or a pharmacologically acceptable salt can be prepared in water suitably mixed with a surfactant, such as hydroxypropylcellulose. A dispersion can also be prepared in glycerol, liquid polyethylene glycols and mixtures thereof and in oils. Under ordinary conditions of storage and use, these preparations may contain a preservative to prevent the growth of microorganisms.

The pharmaceutical forms suitable for injectable use include, for example, sterile aqueous solutions or dispersions and sterile powders for the extemporaneous preparation of sterile injectable solutions or dispersions. In all cases, the form is preferably sterile and fluid to provide easy syringability. It is preferably stable under the conditions of manufacture and storage and is preferably preserved against the contaminating action of microorganisms such as bacteria and fungi. The carrier may be a solvent or dispersion medium containing, for example, water, ethanol, polyol (for example, glycerol, propylene glycol, liquid polyethylene glycol and the like), suitable mixtures thereof, and vegetable oils. The proper fluidity can be maintained, for example, by the use of a coating, such as lecithin, by the maintenance of the required particle size in the case of a dispersion, and by the use of surfactants. The prevention of the action of microorganisms may be achieved by various antibacterial and antifungal agents, for example, parabens, chlorobutanol, phenol, sorbic acid, thimerosal and the like. In many cases, it will be preferable to include isotonic agents, for example, sugars or sodium chloride. Prolonged absorption of the injectable compositions may be achieved by the use of agents delaying absorption, for example, aluminum monostearate and gelatin.

Sterile injectable solutions may be prepared by incorporating the active compound in the required amount, in the appropriate solvent, with various of the other ingredients enumerated above, as required, followed by filtered sterilization. Generally, dispersions may be prepared by incorporating the sterilized active ingredient into a sterile vehicle that contains the basic dispersion medium and the required other ingredients from those enumerated above. In the case of sterile powders for the preparation of sterile injectable solutions, the preferred methods of preparation may include vacuum drying and the freeze drying technique which yield a powder of the active ingredient, plus any additional desired ingredient from the previously sterile-filtered solution thereof.

The therapeutic compounds of this invention may be administered to a patient alone or in combination with a pharmaceutically acceptable carrier. As noted above, the relative proportions of active ingredient and carrier may be determined, for example, by the solubility and chemical nature of the compound, chosen route of administration and standard pharmaceutical practice.

The dosage of the compounds of the present invention that will be most suitable will vary with the form of administration, the particular compound chosen and the physiological characteristics of the particular patient under treatment. Generally, small dosages may be used initially and, if necessary, increased by small increments until the desired effect under the circumstances is reached. The therapeutic human dosage may generally range from about 0.1 mg to about 500 mg/kg of body weight per day, and all combinations and subcombinations of ranges and specific dosages therein. Alternatively, the therapeutic human dosage may be from about 0.5 mg to about 50 g or higher, and all combinations and subcombinations of ranges and specific dosages therein, and may be administered in several different dosage units from once to several times a day. Generally speaking, oral administration may require higher dosages.

EXAMPLES

The invention is further demonstrated in the following examples. All of the examples are actual examples. The examples are for purposes of illustration and are not intended to limit the scope of the present invention.

Materials And Methods

Cell Lines and Reagents. Human umbilical vein endothelial cells ($HUVEC_s$) were obtained from Clonetics (San Diego, Calif.) and cultured in endothelial cell basal medium (EBM) (Clonetics) with 2% heat-inactivated fetal bovine serum (Gibco, Grand Island, N.Y.), 50 µg/ml endothelial cell growth supplement, 50 mg/ml heparin, 10 mM HEPES, and 2 mM L-glutamine. Cells between passages 3 and 8 were used as described below for in vitro capillary tube assays. Porcine aortic endothelial cells (PAEC) were obtained from the American Type Culture Collection (ATCC, Rockville, Md.) and grown in Ham's F-12 medium with 100/o fetal bovine serum and supplements (17) and used between passages 3 and 5 as described below. The SVR angiosarcoma cell line was obtained from the ATCC and maintained as described (18). Cells were MAP-16 and mycoplasma tested by a commercial laboratory (Bio Reliance Corp., Rockville, Md.) and deemed suitable for in vivo studies.

Oltipraz was obtained from Rhone-Poulenc (Vitry-sur-Seine, France) and stored in powdered form in an amber vial at ambient temperature prior to reconstitution in dimethylsulfoxide (DMSO) (for in vitro studies) or Tween:propylene glycol (Tw:PG) (1:1 vol/vol) for oral administration to mice. The anti-angiogenic agent TNP-470 (19) was obtained from Takeda Chemical Industries, Ltd. (Osaka, Japan) and stored dry at −20° C. Suspensions of TNP470 in 5% ethanol and 5% arabic gum in sterile saline were prepared as described (20) prior to oral administration to mice.

Animals. Female athymic nu/nu mice (6–8 weeks old, Charles River, Wilmington, Mass.) were maintained 5/cage in microisolator units on a standard sterilizable laboratory diet (Teklad Labchow, Harlan Teklad, Madison, Wis.). Animals were housed under humidity- and temperature-controlled conditions, and the light/dark cycle was set at 12-h intervals. Mice (22–24 g) were quarantined one week prior to experimental manipulation. Male Sprague-Dawley rats (250–300 g) were obtained from Charles River and housed in a conventional vivarium facility. Male ICR($II_a$.) mice (25 g) were purchased from Taconic Farms (Germantown, N.Y.) and housed at Fox Chase Cancer Center under standard conditions. All in vivo studies were approved by the Institutional Animal Care and Use Committees of the respective institutions.

Example 1

Anti-angiogenic Activity of Oltipraz on Microvessel Growth in Rat Aortic Ring Explant Cultures ex vivo.

Rat aortic ring explant cultures were prepared by a modification of protocols described previously (22–24). This ex vivo model is particularly useful to study microvessel growth, maturation, and remodeling events in the angiogenic process and the role of endothelial cell-adventitial cell interactions in these events (22–24). Briefly, male Sprague-Dawley rats (250 g) were euthanized with $CO_2$ and their thoracic aortas were removed aseptically and carefully to avoid damaging the vessel wall. Aortas were rinsed in serum-free EBM (Clonetics), the surrounding adventitia removed surgically, and the cleaned vessel cut into 1–2 mm concentric rings. Each ring was embedded in freshly prepared rat tail collagen as detailed (24). Following gelation for 30 min at 37° C., collagen gel cultures were transferred to 16 mm wells (4-well NUNC dishes), each containing 0.5 ml of serum-free EBM. Oltipraz was dissolved in DMSO and mixed with serum-free EBM at final concentations of 0.4 µM, 4 µM, 40 µM, and 100 µM immediately prior to the addition of replacement of media to collagen-embedded aortic ring explant cultures. The final DMSO concentration in treated and control cultures was 0.02%. Cultures were incubated at 35.5° C. in a humidified $CO_2$ atmosphere and the media replaced daily over the course of the 8- to 10-day studies. Visual counts of microvessel outgrowths from replicated explant cultures (n=4) were done under bright-field microscopy following an established protocol (24). Experiments were done 3 times, and microvessel counts in Oltipraz-treated and control cultures were analyzed by one-way ANOVA and the Student-Newman-Keuls multiple comparison test, with $p<0.05$ deemed significant.

Figure 1B:
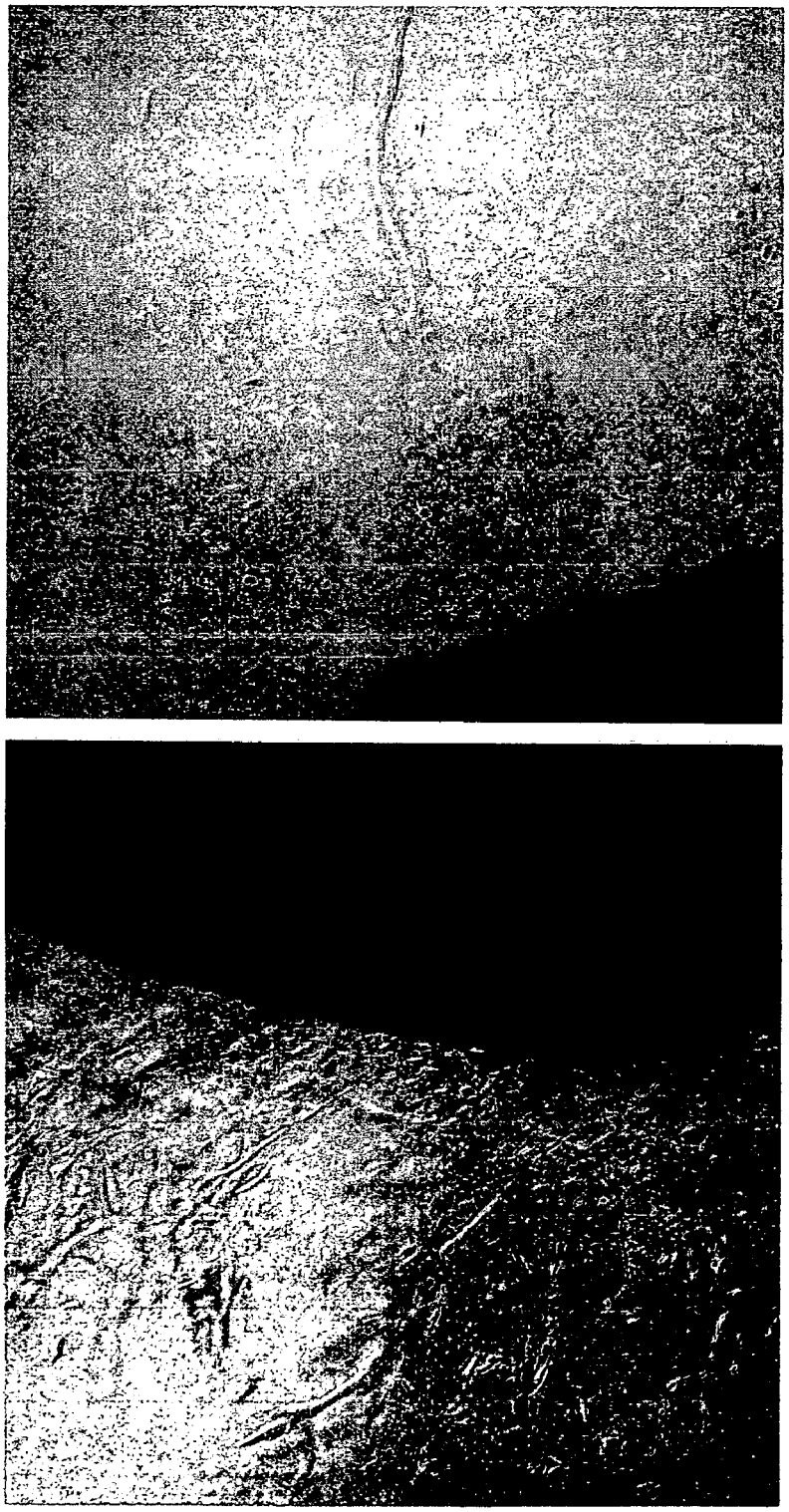

The dose-related effects of Oltipraz on microvessel growth in rat aortic ring explant cultures embedded in collagen gels are shown in FIG. 1. Angiogenesis in this model is a self-limiting physiological process mediated in response to the injury of the aortic dissection process and occurring in the absence of exogenous addition of serum VEGF, or other angiogenic cytokines to the culture medium (29, 30). This assay enables a quantitative assessment of microvessel growth, branching and remodeling, and vessel regression in an explant culture system in which endothelial celladventitial cell interactions critical for angiogenesis in vivo can be effectively modeled in an ex vivo setting. As shown in FIG. 1, administration of 40 µM and 100 µM Oltipraz inhibited microvessel growth by 50% ($p<0.05$) and 95% ($p<0.01$), respectively, relative to vehicle-treated control cultures during the peak (angiogenic) phase of microvessel growth (day 8) in this explant culture assay. Lower concentrations (0.4 µM and 4 µM) were not inhibitory. There were no apparent cytotoxic effects of Oltipraz over the concentration range evaluated on the endothelial cells, fibroblasts, pericytes, and smooth muscle cells present in these aortic ring explant cultures. The inhibition of microvessel growth by Oltipraz was observed over a physiologically relevant range of Oltipraz concentrations capable of inducing phase II detoxification enzymes and inhibiting DNA-carcinogen adduct formation in vitro (13, 15, 16).

Example 2

Anti-angiogenic Activity of Oltipraz on Capillary Tube Formation by HUVECs in vitro.

In order to evaluate the potential anti-angiogenic activity of Oltipraz in a bioassay utilizing human endothelial cells, its ability to inhibit capillary tube formation by HUVECs grown on a Matrigel synthetic extracellular matrix was examined in vitro by a modification of methods described previously (21, 22). This assay models several critical steps in the earlier phases of an in vivo angiogenic response, including endothelial cell adhesion, basement membrane proteolysis, and the proliferation, migration, and differentiation of endothelial cells into a network of capillary tube-like structures—events preceding the formation of new functional microvessels in vivo (21, 22).

Forty-eight-well Nunclon plates (Fisher Scientific, Malvern, Pa.) were coated with Matrigel (Collaborative Research, Bedford, Mass.) (200 µl at 10 mg/ml) and incubated at 37° C. for 30 min to promote gelling. HUVECs were cultured in EBM (Clonetics) with 2% fetal bovine serum (Gibco), and cells between passages 3 and 8 were seeded (at $3 \times 10^4$ cells in 200 µl of medium) in each of the Matrigel-coated wells. Oltipraz was dissolved in DMSO and added to the media in the Matrigel-coated wells at the same time as HUVECs at final concentrations of 4 µM, 40 µM, and 100 µM based upon its aqueous solubility and previously published data (9, 13, 15). The final DMSO concentration in the wells was 0.02%. Following an 18-h incubation at 37° C. in a 5% $CO_2$ humidified atmosphere, HUVECs were aspirated of media, fixed and stained using a modified Wright-Giemsa staining protocol according to the manufacturer's recommendations (Diff-Quik Stain Set, Baxter Healthcare Corp., McGraw Park, EL). Complete capillary tube networks within a designated area of a low magnification (10×) field were counted under light microscopy, and the data were expressed as the percent of complete capillary tube formation relative to untreated HUVEC control cultures incubated under the same conditions. All assays were done in quadruplicate in three independent experiments. Statistical analysis of inhibition of capillary tube formation relative to control cultures was done by the Dunnet's Multiple Comparison test with $p<0.05$ designated as significant. Under these conditions, HUVECs are capable of morphological differentiation into an extensive network of capillary-like structures composed of highly organized three-dimensional cords (31).

Figure 2A:
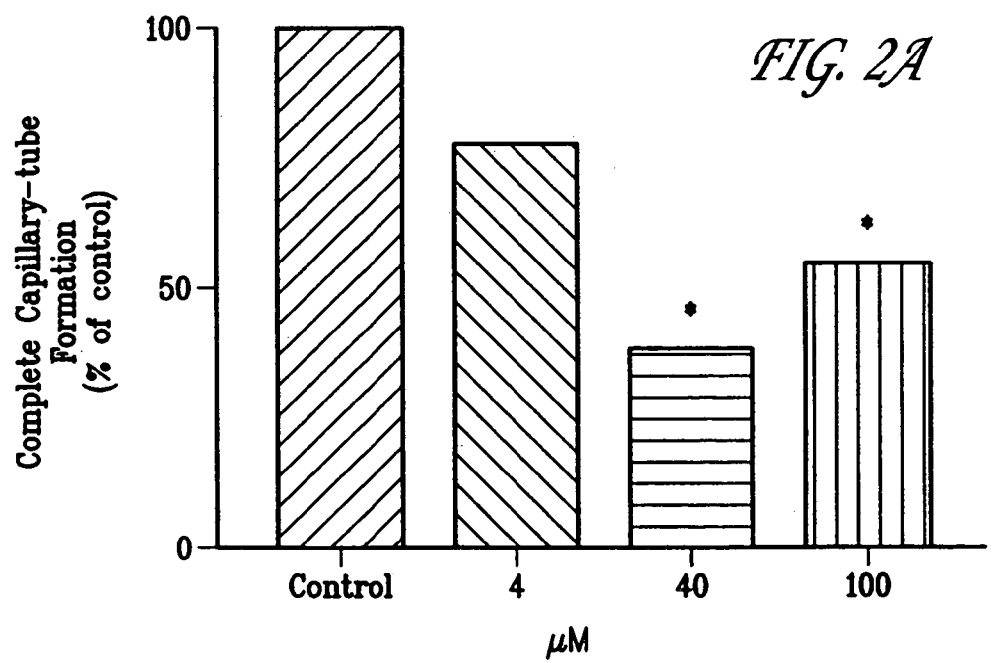
FIG. 2. Effects of Oltipraz on complete capillary-tube formation by human umbilical vein endothelial cells (HUVECs) on Matrigel. A 48-well tissue culture plate was used, and each well was coated with 0.2 ml of Matrigel. Following polymerization of Matrigel at 37° C., HUVECs (30,000 cells/0.2 ml) were added to each well. Oltipraz was added to the media at the tested concentrations. A. After 18 h of incubation, the gels were stained with DiffQuick, and the number of complete tubes was counted in a defined area under phase contrast microscopy. The bars represent the percent tube formation relative to the control. Duplicate experiments were run with 4 replicates. Variation in tube formation was ±5–9% across replicates. *=$p<0.05$ by Dunnet's Multiple Comparison test. B. Light microscopy photographs of HUVEC cultures, vehicle-treated control cultures (left panel) and cultures treated with 100 µM Oltipraz (right panel). Magnification ×100.
Figure 2B:
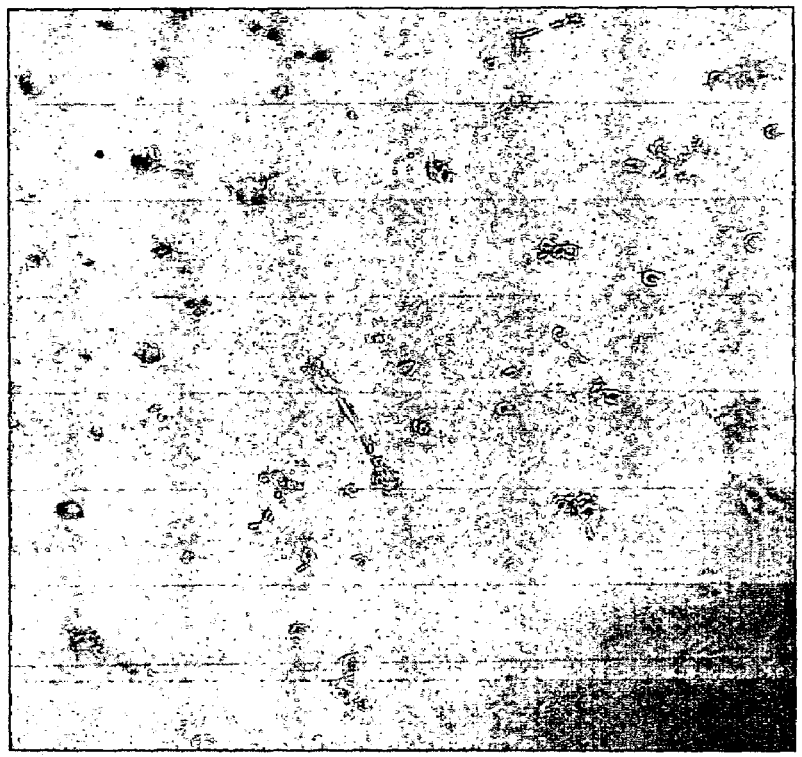
Figure 2B:

As shown in FIG. 2, Oltipraz inhibited complete capillary tube formation by HUVECs by 23%, 62% ($p<0.05$), and 52% ($p<0.05$) relative to vehicle-treated control cultures at concentrations of 4 µM, 40 µM and 100 µM, respectively, in the absence of cytotoxicity to human endothelial cells in culture. The slight reduction in inhibitory activity observed at 100 µM Oltipraz in this assay may have been due to its limited solubility at this concentration under these assay conditions using Matrigel as a matrix. These data substantiate the observations made in rat aortic ring explant cultures for pronounced dose-related inhibition of angiogenesis by Oltipraz in both rodent and human bioassays in the absence of cytotoxicity.

Example 3

In vivo Anti-angiogenic Activity of Orally Administered Oltipraz in the PAEC-Matrigel Plug Assay in Nude Mice.

One approach to the study of angiogenesis in vivo has been the evaluation of neovascularization into biocompatible polymer matrices containing known angiogenic factor(s) or cell types implanted subcutaneously in vivo. This approach has provided a rapid and quantitative means to evaluate the dose-related induction or inhibition of angiogenesis by a variety of stimuli relative to untreated control matrix implants (25, 27, 29). The in vivo inhibition of angiogenesis by orally administered Oltipraz was evaluated in a modified polymer implant assay utilizing PAEC and VEGF in Matrigel injected subcutaneously into athymic nude mice.

The Matrigel plug implantation assay used in these studies was a modification of that described by Passaniti et al. (25). Briefly, PAEC were grown to confluency in Ham's F-12 medium supplemented with 10% fetal bovine serum. Cells were used between passages 5 and 10. Nude mice were injected bilaterally subcutaneously with 0.5 ml Matrigel synthetic basement membrane (Collaorative Research) containing $1 \times 10^6$ PAECs per plug and recombinant murine VEGF (R&D Systems, Minneapolis, Minn.) at 20 ng/ml final concentration per plug. Mice bearing PAEC-VEGF-Matrigel implants were randomized into groups (10/group). Vehicle-treated mice received Tw:PG vehicle (100 µl/dose p.o. QD) by gavage, and Oltipraz-treated mice received 250 mg/kg/dose p.o. QD in the Tw:PG vehicle for a total of 6 days. This oral dosing regimen of Oltipraz was based upon the known pharmacokineic parameters of this agent in rodents and nonhuman primate species (26). Mice were euthanized by $CO_2$ asphyxiation, and the Matrigel plugs were removed and incubated in 0.5 ml Red Cell Lyse (Sigma Diagnostics. St. Louis, Mo.) at 37° C. overnight. Individual plugs were minced in eppendorf tubes, briefly microfuged and the resultant supernatant analyzed colorimetrically for its hemoglobin concentration using the Drabkin method (Sigma Diagnostics) as described (25, 27). The contralateral plug from each mouse was evaluated histologically for vessel morphology as described (25). Briefly, the Drabkin procedure is based on the oxidation of hemoglobin to methemoglobin in the presence of alkaline potassium ferricyanide. Methemoglobin reacts with potassium cyanide to form cyanmethemoglobin with a maximum absorption of 540 nm. Supernatant from each Matrigel plug (100 µl) was mixed with 1 ml of Drabkin's solution (Sigma) and the hemoglobin content was analyzed spectrophotometrically at 540 nm. The hemoglobin content of the PAEC-VEGF-Matrigel plugs has been reported to be directly proportional to the degree of neovascularization in each plug (25, 27). Results from duplicate in vivo experiments are expressed as mean g/dl of hemoglobin±standard error of the mean (SEM). Statistical analyses of the data were done using the Paired Student's t-test with $p<0.05$ deemed significant.

Figure 3:
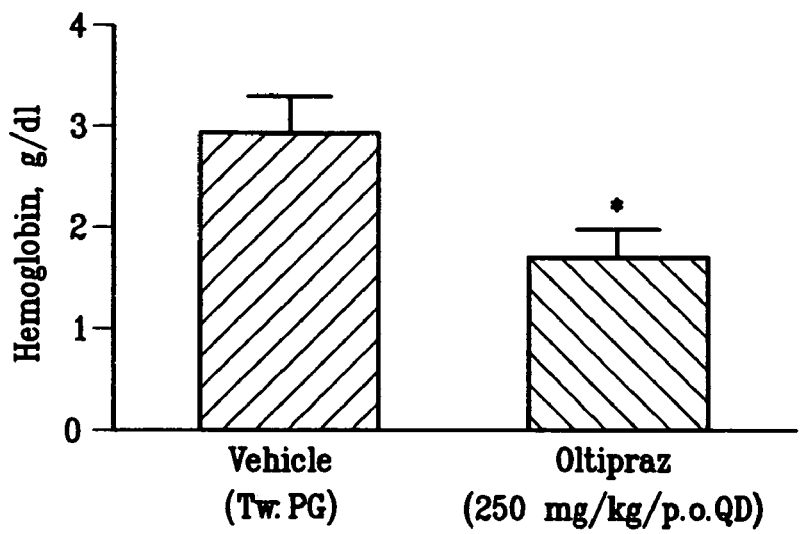
FIG. 3. Effects of oral Oltipraz administration on angiogenesis in vivo in the PAEC-VEGF-Matrigel implant model. Female athymic nude mice were injected bilaterally s.c. with Matrigel containing $1\times10^6$ PAEC and 20 ng/ml of recombinant murine vascular endothelial growth factor (VEGF). Implanted mice were administered Oltipraz by oral gavage at 250 mg/kg/dose QD in a Tw:PG vehicle (100 microliters/dose). Six days postdosing, implants were excised and evaluated for the extent of neovascularization calorimetrically (540 nm) on the basis of hemoglobin content (Drabkin method) as detailed in Example 3. Results from two independent experiments (n=10 mice/group in each) are expressed as mean g/dl of hemoglobin ±SEM. *$p<0.05$.

Oltipraz was administered at 250 mg/kg/dose per os once a day in a TW:PG vehicle based upon its pharmacokinetic profile in mice in order to achieve sustained plasma concentrations in a physiologically relevant (µM) range over a 6- to 24-h period (26). The determination of the extent of angiogenesis within the implanted matrix was based on the quantization of the hemoglobin content of the vascularized implants upon removal from the host. As shown in FIG. 3, oral administration of Oltipraz for 6 days resulted in a 42% reduction in neovascularization ($p<0.05$) relative to TW:PG vehicle-treated control mice over the same time course. These results were observed in the absence of apparent toxicity or morbidity as assessed by body weight loss in nude mice (data not shown). These observations are in accord with previous reports of the tolerability of Oltipraz administration in rodents (7), and demonstrate the significant oral anti-angiogenic efficacy of Oltipraz in an established in vivo bioassay of physiologic angiogenesis (25, 27).

Example 4

Anti-tumor Efficacy of Oral Oltipraz Administration on Established Murine SVR Angiosarcoma Xenografts in Athymic Nude Mice.

The SVR angiosarcoma is a highly aggressive endothelial cell tumor with a high take rate and short latency period that is generally refractory to standard treatment regimens and results in the death of the host animal from local invasiveness and hemorrhage (18, 28). Due to the nature of this tumor model, inhibition of its growth is likely to reflect both anti-angiogenic activities on the host endothelium and anti-tumor activity on the angiosarcoma cells directly (28).

SVR cells are primary murine pancreatic Islet-derived endothelial cells immortalized and transformed by the sequential introduction of SV 40 large T antigen and activated H-ras, respectively (18). These cells give rise to highly aggressive angiosarcomas in athymic mice with a short latency period, and result in a high mortality rate within several weeks post-implantation, as a result of local invasion and hemorrhage. The use of this model to study the regulation of tumor angiogenesis and the antitumor efficacy of anti-angiogenic agents has been described (18, 28).

Cultures of murine SVR cells (in Dulbecco's Modified Eagle Medium (DNEM) supplemented with 10% fetal calf serum) were grown to subconfluency. SVR cells were injected subcutaneously into the right flank of female athymic nude mice at $1\times10^6$ cells per mouse in serum-free DNEM. At day 6 post-implantation when palpable growing tumors (95±5 $mm^3$) were confirmed, mice were randomized into treatment groups (10 mice/group). Oral administration of Oltipraz and the TW:PG vehicle was done according to the dosing regimen described above in evaluating angiogenesis inhibition in vivo in the PAEC-VEGF-Matrigel implant model and for a total of 10 days. The fumagillin analogue TNP-470 (19, 28) was evaluated in this angiosarcoma model as a reference anti-angiogenic agent. Tumor volumes were determined with vernier calipers every 3 to 4 days; and both absolute tumor volumes and relative tumor volumes (normalized to individual tumor volumes at the initiation of dosing) were calculated, the latter to assess changes in the rate of tumor growth with treatment. Statistical analyses of tumor data were done using the Mann-Whitney Rank Sum test, or when appropriate for the data set, by one-way ANOVA and the Dunnet's Multiple Comparison test with $p<0.05$ deemed significant.

Figure 4:
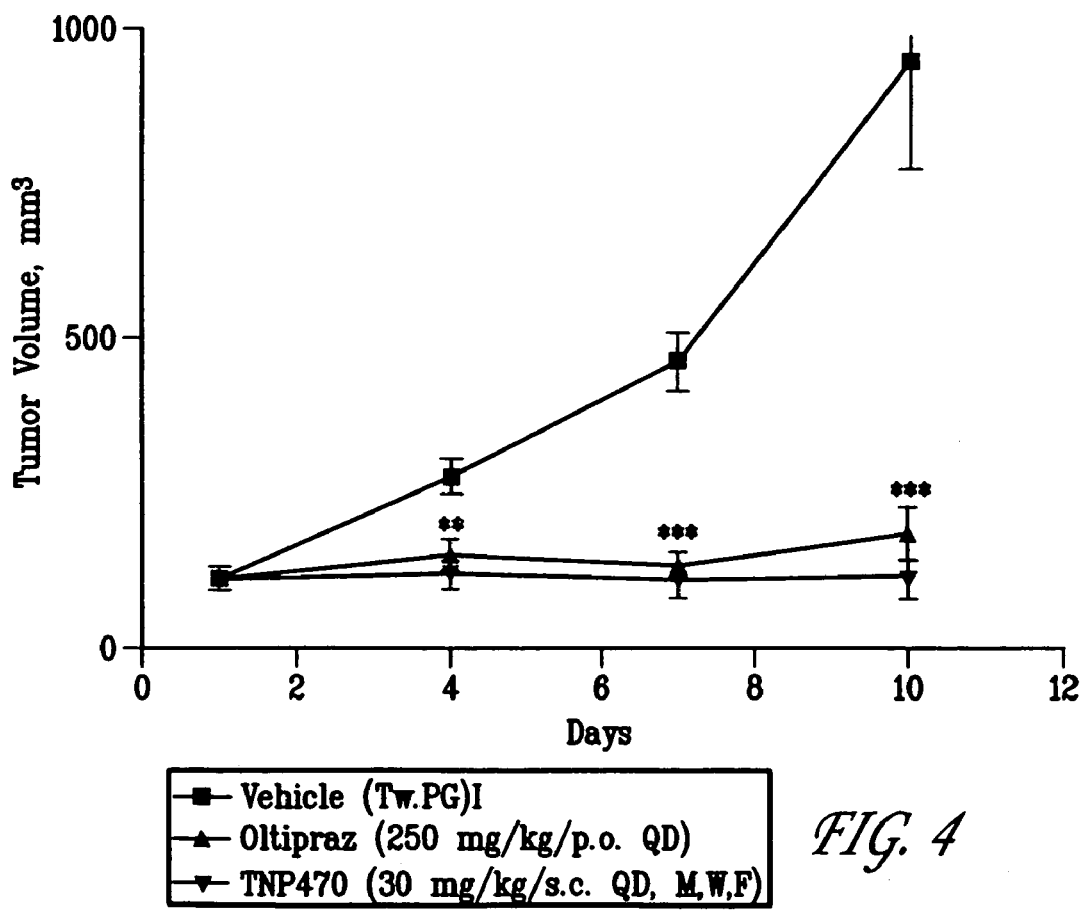
FIG. 4. Murine endothelial SVR cells ($1\times10^6$) were injected into the right flank of female nu nu athymic nude mice. At day 6 postimplantation when palpable tumors were confirmed, mice were randomized into vehicle and treatment groups (n=9) and the compound was administered. Oltipraz was made up in a 1:1 Tw:PG vehicle, and animals were dosed orally by gavage once a day at a concentration of 250 mg/kg/dose. Statistical analyses were done using the Mann-Whitney Sum Test with =$p<0.05$ and *=$p<0.001$.

Oral administration of Oltipraz at the same dose (250 mg/kg/dose p.o. QD), shown to be anti-angiogenic in the Matrigel plug implant model (FIG. 3), was initiated in athymic mice bearing established subcutaneous SVR angiosarcoma xenografts (95±5 $mm^3$ 6 days post-implantation) and continued for a total of 10 days. As shown in FIG. 4, Oltipraz administration resulted in a significant inhibition of tumor growth as early as day 4 of dosing ($p<0.005$) with a maximum inhibition of tumor volume (81%, $p<0.001$) relative to TW:PG vehicle-treated mice by day 10 of the dosing regimen. These effects were observed in the absence of apparent morbidity or mortality to the Oltipraz-treated mice. By comparison, administration of TNP-470 (30 mg/kg/dose s.c. Q2Dx3 (20, 28)) in the same model over the same time course resulted in an 80% maximum reduction in SVR tumor volume, relative to vehicle-treated control mice by day 10 (FIG. 4). These results with TNP-470 administration in this tumor model are in agreement with published accounts (28). These findings indicate that oral administration of Oltipraz has an anti-tumor efficacy in the highly aggressive and angiogenic SVR angiosarcoma model comparable to that of an established anti-angiogenic agent currently under clinical evaluation.

In summary, these data demonstrate that 1,2-dithiol-3-thione derivatives such as Oltipraz have potent anti-angiogenic activity at physiologic concentrations that were previously shown to have minimal toxicity in humans. This anti-angiogenic activity was observed in vitro, ex vivo and in vivo. In view of its previously established pharmaceutical properties as a prototypic chemopreventive agent and its favorable therapeutic index in rodents and humans, these compounds are well suited for use as chemotherapeutic anti-angiogenic agents in clinical applications.

REFERENCES

1. Gasparini, G. (1999) *Drugs* 58, 17–38.
2. Hanahan, D. (1997) *Science* 277, 48–50.
3. Griffioen, A. W. & Molema, G. (2000) *Pharmacol. Rev.* 52, 237–268.
4. Folkman, J. (2000) in *Cancer Medicine,* 5th Edition, eds. Holland, J. E. E. Frei, I. R. Bast, J. Kufe, D. Pollock, R. & Weichselbaum, R. (B. C. Dekker, Inc., Ontario, Canada), pp. 132–152.
5. Deplanque, G. & Harris, A. L. (2000) *Eur. J Cancer* 36, 1713–1724.
6. Kensler, T. W. & Helzlsouer, K. J. (1995) *J. Cell. Biochem.* 22(S), 101–107.
7. Clapper, M. L. (1998) *Pharmacol. Ther.* 78, 17–27.
8. Bueding, E., Dolan, P. & Leroy, J. P. (1982) *Res. Comm. Chem. Path. Pharm.* 37, 293–303.
9. Elmore, E., Luc, T. T., Li, H. R., Buckmeier, J. A., Steele, V. E., Kelloff, G. J. & Redpath, J. L. (2000) *Anticancer Res.* 20, 27–32.
10. Ansher, S. S., Dolan, P. & Bueding, E. (1986) *Food Chem. Toxicol.* 24, 405–415.
11. Kensler, T. W., Egner, P. A., Dolan, P. M., Groopman, J. D. & Roebuck, B. D. (1987) *Cancer Res.* 47, 4271–4277.
12. Clapper, M. L., Everley, L. C., Strobel, L. A., Townsend, A. J. & Engstrom, P. F. (1994) *Mol. Pharmacol.* 45, 469–474.
13. O'Dwyer, P. J., Johnson, S. W., Khater, C., Krueger, A., Matsumoto, Y., Hamilton, T. C. & Yao, K.-S. (1997) *Cancer Res.* 57, 1050–1053.
14. Liu, Y.-L., Roebuck, B. D., Yager, J. D., Groopman, J. D. & Kensler, T. W. (1988) *Toxicol. Appl. Pharmacol.* 93, 442–451.
15. O'Dwyer, P. J., Clayton, M., Halbherr, T., Myers, C. B. & Yao, K. S. (1997) *Clin. Cancer Res.* 3, 783–791.
16. Smith, W. A., Freeman, J. W. & Gupta, R. C. (1997) *Proc. Am. Assoc. Cancer Res.* 38, 362.
17. Bernatchez, P. N., Soker, S. & Sirois, M. G. (1999) *J. Biol. Chem.* 274, 31047–31054.
18. Arbiser, J. L., Moses, M. A., Fernandez, C. A., Ghiso, N., Cao, Y., Klauber, N., Frank, D., Brownlee, M., Flynn, E., Parangi, S., et al. (1997) *Proc. Natl. Acad Sci. USA* 94, 861–866.
19. Ingber, D., Fujita, T., Kishimoto, S., Sudo, K., Kanamaru, T., Brem, H. & Folkman, J. (1990) *Nature* 348, 555–557.
20. Liekens, S., Verbeken, E., Vandeputte, M., De Clercq, E. & Neyts, J. (1999) *Cancer Res.* 59, 2376–2383.
21. Ilan, N., Mahooti, S. & Madri, J. A. (1998) *J Cell Sci.* 111, 3621–3631.
22. Malinda, K. M., Nomizu, M., Chung, M., Delgado, M., Kuratomi, Y., Yamada, Y., Kleinman, H. K. & Ponce, M. L. (1999) *FASEB J.* 13, 53–62.

23. Brown, K. J., Maynes, S. F., Bezos, A., Maguire, D. J., Ford, M. D. & Parish, C. R. (1996) *Lab Invest.* 75, 539–555.
24. Nicosia, R. F., Lin, Y. J., Hazelton, D. & Qian, X. (1997) *Am. J. Pathol.* 151, 1379–1386.
25. Passaniti, A., Taylor, R. M., Pili, R., Guo, Y., Long, P. V., Haney, J. A., Pauly, R. R., Grant, D. S. & Martin, G. R. (1992) *Lab Invest.* 67, 519–528.
26. Heusse, D., Malard, M., Bredenbac, J., Decouvelaere, B., Leroy, J. P., Bieder, A. & Jumeau, H. (1985) *Arzneimittelforschung* 35, 1431–1436.
27. Plunkett, M. L. & Hailey, J. A. (1990) *Lab Invest.* 62, 510–517.
28. Arbiser, J. L., Panigrathy, D., Klauber, N., Rupnick, M., Flynn, E., Udagawa, T. & D'Amato, R. J. (1999) *J. Am. Acad. Dermatol.* 40, 925–929.
29. Nicosia, R. F. & Villaschi, S. (1999) *Int Rev. Cytol.* 185, 1–43.
30. Zhu, W. H., Guo, X., Villaschi, S. & Nicosia, R. F. (2000) *Lab Invest.* 80, 545–555.
31. Montesano, R., Orci, L. & Vassalli, P. (1983) *J Cell Biol.* 97, 1648–1652.
32. Jain, R. K., Schlenger, K., Hockel, M. & Yuan, F. (1997) *Nature Med* 3, 1203–1208.
33. Bieder, A., Decouvelaire, B., Gaillard, C., Depaire, H., Heusse, D., Ledoux, C., Lemar, M., Le Roy, J. P., Raynaud, L., Snozzi, C., & Gregoire, J., (1983) *Drug Res* 33(11), 1289–1297.

The disclosures of each patent, patent application and publication cited or described in this document are hereby incorporated herein by reference, in their entirety.

Various modifications of the invention, in addition to those described herein, will be apparent to those skilled in the art from the foregoing description. Such modifications are also intended to fall within the scope of the appended claims.

What is claimed is:

1. A method for inhibiting angiogenesis in a patient comprising administering to said patient an anti-angiogenically effective amount of a 1,2-dithiol-3-thione derivative selected from the group consisting of 5-(2-pyrazinyl)-1,2-diothiol-3-thione (ADT), and 5-(2-pyrazinyl)-4-methyl-1,2-diothiol-3-thione or a metabolite thereof and determining the anti-angiogenic effect on said patient produced by said derivative or metabolite thereof.

2. The method according to claim 1 wherein said 1,2-dithiol-3-thione derivative is 5-(2-pyrazinyl)-4-methyl-1,2-dithiol-3-thione.

3. A method for inhibiting the growth or metastasis of an angiogenesis-dependent tumor in a patient comprising administering to said patient an effective amount of an anti-angiogenic agent, wherein said anti-angiogenic agent comprises a compound of the following formula (I):

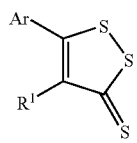

wherein:
Ar is a monocyclic or bicyclic aryl group or a monocyclic or bicyclic heteroaryl group containing 1 to 3 —O—, —S— or N($R^2$)$_m$ heteroatoms, wherein m is 0 or 1; and
$R^1$ and $R^2$ are independently hydrogen or an alkyl group; or a steroisomer, prodrug, metabolite, or pharmaceutically acceptable salt, hydrate or N-oxide thereof and determining the anti-angiogenic effect on said tumor produced by said compound.

4. The method according to claim 3 wherein Ar is a monocyclic or bicyclic heteroaryl group containing 1 to 3 oxygen, sulfur or nitrogen heteroatoms.

5. The method according to claim 4 wherein Ar is a monocylic heteroaryl group containing 1 to 2 nitrogen atoms.

6. The method according to claim 5 wherein Ar is selected from the group consisting of pyridyl, pyridazinyl, pyrimidinyl and pyrazinyl.

7. The method according to claim 6 wherein Ar is pyrazinyl.

8. The method according to claim 3 wherein $R^1$ is hydrogen.

9. The method according to claim 3 comprising administering to said patient a metabolite of the compound of formula (I).

10. The method according to claim 9 wherein said metabolite has the following formula (II):

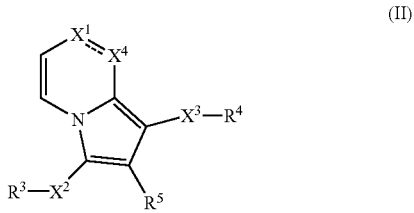

wherein:
$X^1$ is C($R^6$)$_y$ or N($R^7$)$_n$ in which y is an integer 1 or 2, and n is an integer 0 or 1;
$X^2$ and $X^3$ are each independently —O—, —S(O)$_x$— where x is an integer 0, 1 or 2, or —N($R^8$);
$X^4$ is C($R^6$)$_y$ or C(=O), in which y is an integer 1 or 2;
$R^3$ is hydrogen, alkyl, the residue of glucuronic acid, or the radical

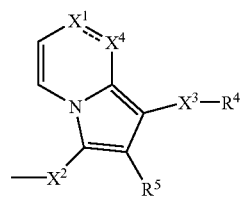

$R^4$, $R^5$ and $R^6$ are each independently hydrogen or alkyl;
$R^7$ is hydrogen or the residue of glucuronic acid;
$R^8$ is hydrogen or alkyl; and $X^1$, $X^2$, $X^3$ and $X^4$ are as previously defined.

11. The method according to claim 10 wherein:
$X^1$ is N;
$X^2$ and $X^3$ are —S—; and
$R^3$, $R^4$ and $R^5$ are methyl.

12. The method according to claim 3, wherein said anti-angiogenic effect is determined by measuring the tumor burden in said patient.

13. A method for inhibiting the growth or metastasis of an angiogenesis-dependent tumor in a patient comprising administering to said patient an effective amount of an anti-angiogenic agent, wherein said anti-angiogenic agent comprises a 1,2-dithiol-3-thione derivative selected from the group consisting of 5-(2-pyrazinyl)-1,2-diothiol-3-thione (ADT), and 5-(2-pyrazinyl)-4-methyl-1,2-diothiol-3-thione or a metabolite thereof and determining the anti-angiogenic effect on said tumor produced by said 1,2-diothiol-3-thione derivative or metabolite thereof.

14. The method according to claim 13 wherein said 1,2-dithiol-3-thione derivative is 5-(2-pyrazinyl)-4-methyl-1,2-dithiol-3-thione.

15. The method according to claim 13, wherein said anti-angiogenic effect is determined by measuring the tumor burden in said patient.

16. A method for treating a disease or disorder associated with angiogensesis in a patient, said disease or disorder being selected from the group consisting neoplastic diseases, restenosis, rheumatoid arthritis, Crohn's disease, diabetic retinopathy, psoriasis, endometriosis, macular degeneration, neovascular glaucoma, and adiposity, comprising administering to said patient an effective amount of an anti-angiogenic agent, wherein said anti-angiogenic agent comprises a compound of the following formula (I):

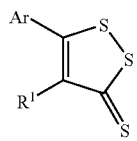

(I)

wherein:
Ar is a monocyclic or bicyclic aryl group or a monocyclic or bicyclic heteroaryl group containing 1 to 3 —O—, —S— or —N(R2)m heteroatoms, wherein m is 0 or 1; and
R1 and R2 are independently hydrogen or an alkyl group; or a steroisomer, prodrug, metabolite, or pharmaceutically acceptable salt, hydrate or N-oxide thereof and determining the anti-angiogenic effect on said patient produced by said compound.

17. The method according to claim 16 wherein Ar is a monocyclic or bicyclic heteroaryl group containing 1 to 3 oxygen, sulfur or nitrogen heteroatoms.

18. The method according to claim 17 wherein Ar is a monocylic heteroaryl group containing 1 to 2 nitrogen atoms.

19. The method according to claim 18 wherein Ar is selected from the group consisting of pyridyl, pyridazinyl, pyrimidinyl and pyrazinyl.

20. The method according to claim 19 wherein Ar is pyrazinyl.

21. The method according to claim 16 wherein R$^1$ is hydrogen.

22. The method according to claim 16 comprising administering to said patient a metabolite of the compound of formula (I).

23. The method according to claim 22 wherein said metabolite has the following formula (II):

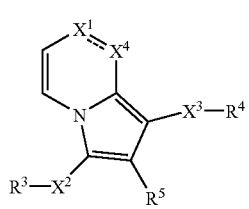

(II)

wherein:
X$^1$ is C(R$^6$)$_y$ or N(R$^7$)$_n$ in which y is an integer 1 or 2, and n is an integer 0 or 1;
X$^2$ and X$^3$ are each independently —O—, —S(O)$_x$— where x is an integer 0, 1 or 2, or —N(R$^8$);
X$^4$ is C(R$^6$)$_y$ or C(=O), in which y is an integer 1 or 2;
R$^3$ is hydrogen, alkyl, the residue of glucuronic acid, or the radical

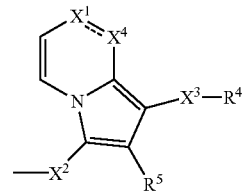

R$^4$, R$^5$ and R$^6$ are each independently hydrogen or alkyl;
R$^7$ is hydrogen or the residue of glucuronic acid;
R$^8$ is hydrogen or alkyl and X$^1$, X$^2$, X$^3$ and X$^4$ are as previously defined.

24. The method according to claim 23 wherein:
X$^1$ is N;
X$^2$ and X$^3$ are —S—; and
R$^3$, R$^4$ and R$^5$ are methyl.

25. The method according to claim 16, wherein said disease or disorder is a neoplastic disease.

26. The method according to claim 25, wherein said neoplastic disease is cancer.

27. The method according to claim 25, wherein said an anti-angiogenic effect is determined on the basis of neoplasm regression.

28. The method according to claim 27, wherein neoplasm regression is demonstrated by reduced size.

29. The method according to claim 27, wherein neoplasm regression is demonstrated by reduced neoplasm number.

30. The method according to claim 25, wherein said anti-angiogenic effect is determined on the basis of reduced neovascularization.

31. A method for treating a disease or disorder associated with angiogenesis in a patient, said disease or disorder being selected from the group consisting of neoplastic diseases, restenosis, rheumatoid arthritis, Crohn's disease, diabetic retinopathy, psoriasis, endometriosis, macular degeneration, neovascular glaucoma, and adiposity, comprising administering to said patient an effective amount of an anti-angiogenic agent, wherein said anti-angiogenic agent comprises a 1,2-dithiol-3-thione derivative selected from the group consisting of 5-(2-pyrazinyl)1,2-diothiol-3-thione (APT), and 5-(2-pyrazinyl)-4-methyl-1,2-diothiol-3-thione or a metabolite thereof and determining the anti-angiogenic effect on said patient produced by said 1,2-dithiol-3-thione derivative or metabolize thereof.

32. The method according to claim 31 wherein said 1,2-dithiol-3-thione derivative is 5-(2-pyrazinyl)-4-methyl-1,2-dithiol-3-thione.

* * * * *